(12) United States Patent
Chia et al.

(10) Patent No.: US 9,763,736 B2
(45) Date of Patent: *Sep. 19, 2017

(54) LASER PROBE TIP

(71) Applicant: AMS Research, LLC, Minnetonka, MN (US)

(72) Inventors: Wen-Jui Ray Chia, Sunnyvale, CA (US); Meiling Wu, San Jose, CA (US); Ion Ghinea, Fremont, CA (US); Ming Ko, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 853 days.

This patent is subject to a terminal disclaimer.

(21) Appl. No.: 14/146,917

(22) Filed: Jan. 3, 2014

(65) Prior Publication Data

US 2014/0121655 A1    May 1, 2014

Related U.S. Application Data

(63) Continuation of application No. 13/326,813, filed on Dec. 15, 2011, now Pat. No. 8,672,929.

(Continued)

(51) Int. Cl.
*A61B 18/22* (2006.01)

(52) U.S. Cl.
CPC ...... *A61B 18/22* (2013.01); *A61B 2018/2272* (2013.01); *Y10T 29/4902* (2015.01); *Y10T 29/49929* (2015.01)

(58) Field of Classification Search
CPC ............ A61B 18/22; A61B 2018/2272; Y10T 29/49929; Y10T 29/4902
See application file for complete search history.

(56) References Cited

U.S. PATENT DOCUMENTS 5,061,265 A    10/1991    Abela et al.
5,246,436 A     9/1993    Rowe
(Continued)

FOREIGN PATENT DOCUMENTS

EP    1727249    11/2006
JP    60-250322    12/1985
(Continued)

OTHER PUBLICATIONS

International Search Report and Written Opinion for PCT/US2007/024963, filed Dec. 6, 2007.
(Continued)

*Primary Examiner* — Gary Jackson
*Assistant Examiner* — Scott T Luan
(74) *Attorney, Agent, or Firm* — Brookoff McAndrews, PLLC

(57) ABSTRACT

A probe tip for communicating and laterally directing electromagnetic radiation comprises a waveguide, a primary capsule, a compressible member and a malleable secondary capsule. The waveguide is configured to communicate electromagnetic radiation and includes a beveled surface at a distal tip for redirecting electromagnetic radiation in a lateral direction. The primary capsule is attached over the distal tip of the waveguide. The compressible member covers a portion of the primary capsule. The malleable secondary capsule is positioned over the primary capsule and the compressible member, and includes a crimp that compresses the compressible member against the primary capsule and secures the secondary capsule to the primary capsule.

26 Claims, 8 Drawing Sheets

Related U.S. Application Data

(60) Provisional application No. 61/423,461, filed on Dec. 15, 2010, provisional application No. 61/423,371, filed on Dec. 15, 2010.

(56) References Cited

U.S. PATENT DOCUMENTS

| | | | |
|---|---|---|---|
| 5,343,543 | A | 8/1994 | Novak, Jr. et al. |
| 5,428,699 | A | 6/1995 | Pon |
| 5,509,917 | A | 4/1996 | Cecchetti et al. |
| 5,537,499 | A | 7/1996 | Brekke |
| 5,629,952 | A | 5/1997 | Bartholomew et al. |
| 5,772,657 | A | 6/1998 | Hmelar et al. |
| 5,882,773 | A | 3/1999 | Chow et al. |
| 5,957,917 | A | 9/1999 | Doiron et al. |
| 6,238,104 | B1 * | 5/2001 | Yamakawa .......... G02B 6/3869 385/81 |
| 6,554,824 | B2 | 4/2003 | Davenport et al. |
| 6,802,838 | B2 | 10/2004 | Loeb et al. |
| 6,986,764 | B2 | 1/2006 | Davenport et al. |
| 7,063,694 | B2 | 6/2006 | Nahen et al. |
| 7,447,409 | B2 | 11/2008 | Griffin |
| 7,909,817 | B2 | 3/2011 | Griffin et al. |
| 8,672,929 | B2 | 3/2014 | Anderson et al. |
| 2002/0018633 | A1 | 2/2002 | Imaizumi |
| 2003/0011872 | A1 | 1/2003 | Shull |
| 2003/0099266 | A1 | 5/2003 | Watanabe et al. |
| 2003/0227957 | A1 | 12/2003 | Pang |
| 2004/0109650 | A1 | 6/2004 | Kim et al. |
| 2007/0185474 | A1 | 8/2007 | Nahen |
| 2009/0048588 | A1 * | 2/2009 | Peng ..................... A61B 18/22 606/16 |
| 2009/0105698 | A1 | 4/2009 | Hodel et al. |
| 2010/0061412 | A1 | 3/2010 | Reed et al. |
| 2010/0135617 | A1 | 6/2010 | Novak et al. |
| 2011/0176772 | A1 | 7/2011 | Hixon et al. |
| 2011/0230872 | A1 | 9/2011 | Griffin et al. |
| 2012/0316546 | A1 * | 12/2012 | Appling ................. A61B 18/24 606/15 |

FOREIGN PATENT DOCUMENTS

| | | |
|---|---|---|
| JP | 62-011820 | 1/1987 |
| JP | 2001281551 | 10/2001 |
| JP | 2003298171 | 10/2003 |
| WO | 2008/073263 | 6/2008 |
| WO | 2010/014787 | 2/2010 |
| WO | 2010/075254 | 7/2010 |

OTHER PUBLICATIONS

International Search Report and Written Opinion for PCT/US2009/068933, filed Dec. 21, 2009.

International Search Report and Written Opinion for PCT/US2009/052214, filed Jul. 30, 2009.

Maruno, T. et al., "Fluorine-Containing Optical Adhesives for Optical Communications Systems," Journal of Applied Polymer Science, Jon Wiley and Sons, Inc., NY vol. 42, No. 8, Apr. 20, 1991, pp. 2141-2148.

Nakamura, K. et al., "Design and Development of Optical Adhesives for Optical Communications," Review of the Electrical Communication Laboratories, Mushino Electrical Communication Laboratory, Tokyo, JP, vol. 37, No. 2, Mar. 1, 1989, pp. 127-132.

Prosecution documents from corresponding U.S. Appl. No. 13/326,813; including: Non-Final Office Action, mailed Mar. 12, 2013 and Final Office Action, mailed Aug. 12, 2013.

* cited by examiner

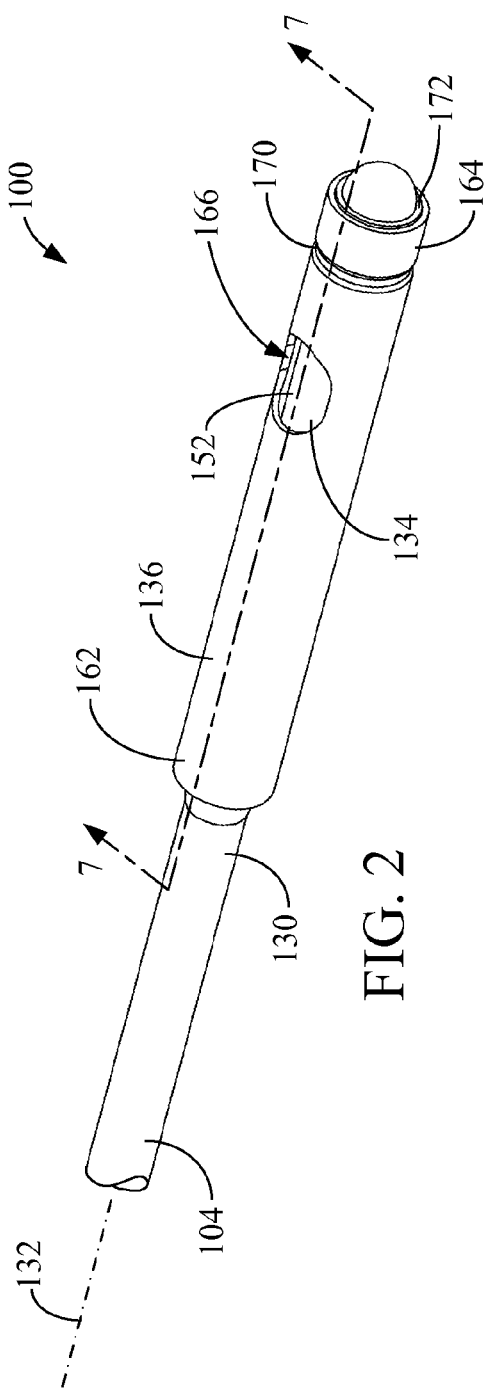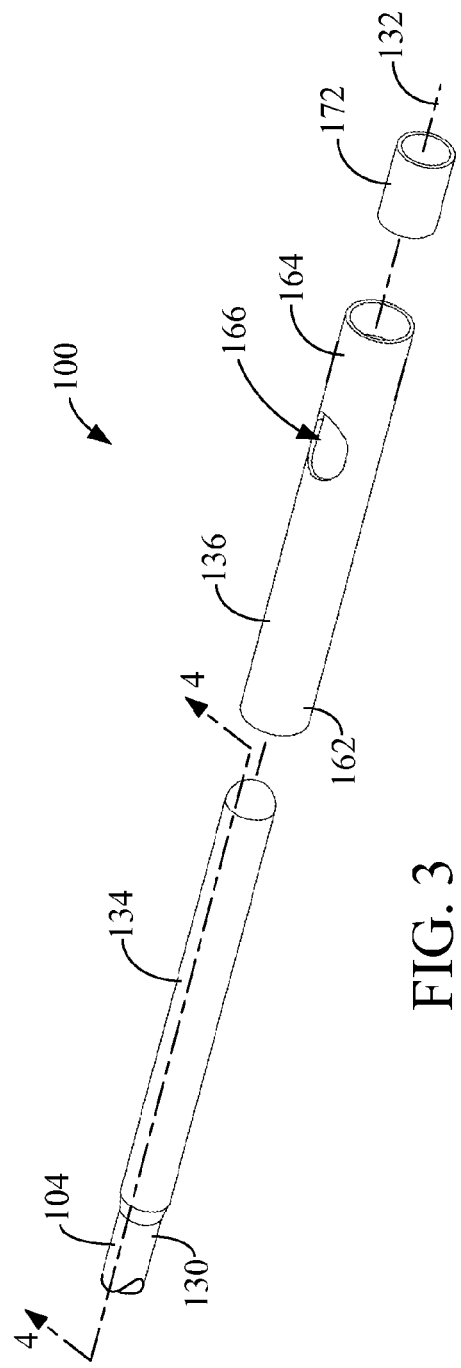
FIG. 2
FIG. 3

LASER PROBE TIP

CROSS-REFERENCE TO RELATED APPLICATION

The present application is a continuation of U.S. patent application Ser. No. 13/326,813, filed Dec. 15, 2011, which is based on and claims the benefit of U.S. provisional patent application Ser. No. 61/423,461, filed Dec. 15, 2010; and U.S. provisional patent application Ser. No. 61/423,371, filed Dec. 15, 2010. The content of each of the above-identified applications is hereby incorporated by reference in their entirety.

FIELD

Embodiments of the invention are directed to a probe tip for use in medical laser treatments by communicating and laterally directing electromagnetic radiation and methods of forming the probe tip.

BACKGROUND

Medical lasers have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of energy as part of the treatment protocol.

Many tissue-ablative laser systems, such as the American Medical Systems GREENLIGHT® Laser System, utilize a frequency-doubled Nd:YAG laser operating at 532 nm. This wavelength, provided in a quasi-continuous mode, is used at high power levels for efficient tissue ablation. The frequency doubled Nd:YAG laser can be pumped by CW krypton arc lamps and can produce a constant train of laser light pulses. When ablative power densities are used, a superficial layer of denatured tissue is left behind. At high powers, 532 nm lasers induce a superficial char layer that strongly absorbs the laser light and improves ablation efficiency.

Many surgical laser procedures utilize a surgical probe, which generally comprises an optical fiber and a fiber cap over a distal end of the optical fiber to form a probe tip. A laser source delivers laser energy through the optical fiber to the probe tip where the energy is discharged through the fiber cap and onto desired portions of the targeted tissue.

The laser energy may be directed laterally from the probe tip by reflecting the laser energy off a polished beveled surface at the distal end of the optical fiber. The fiber cap seals a cavity containing a gas (or vacuum) that maintains the necessary refractive index difference for total internal reflection at the beveled surface.

The fiber cap may be protected from tissue adhesion and other causes of fiber cap degradation by surrounding the fiber cap with a second cap, as described in U.S. Pat. No. 7,909,817, which is incorporated by reference herein in its entirety.

There is a continuous need for improvements in laser fiber probe tips, such as improvements that reduce manufacturing costs and increase reliability. Embodiments described herein provide solutions to these and other problems, and offer other advantages over the prior art.

SUMMARY

Embodiments of the invention are directed to a probe tip for use in medical laser treatments by communicating and laterally directing electromagnetic radiation. In one embodiment, the probe tip comprises a waveguide, a primary capsule, a compressible member and a malleable secondary capsule. The waveguide is configured to communicate electromagnetic radiation and includes a beveled surface at a distal tip for redirecting electromagnetic radiation in a lateral direction. The primary capsule is attached over the distal tip of the waveguide. The compressible member covers a portion of the primary capsule. The malleable secondary capsule is positioned over the primary capsule and the compressible member, and includes a crimp that compresses the compressible member against the primary capsule and secures the secondary capsule to the primary capsule.

In accordance with another embodiment, the probe tip comprises an optical fiber, a primary capsule and a secondary capsule. The optical fiber comprises a core for communicating electromagnetic radiation and a protective layer surrounding the core. The core comprises a distal tip that extends beyond the protective layer and includes a beveled surface for redirecting electromagnetic radiation in a lateral direction. The primary capsule is attached over the distal tip of the core. The secondary capsule is positioned over the primary capsule and includes a proximal end having a crimp that compresses the protective layer of the optical fiber and secures the position of the secondary capsule relative to the primary capsule.

Yet another embodiment is directed to a method. In the method, a waveguide is provided for communicating electromagnetic radiation. The waveguide includes a beveled surface at a distal tip for redirecting electromagnetic radiation in a lateral direction. A primary capsule is attached over the distal tip of the waveguide. A compressible member is placed on a portion of the primary capsule. A malleable secondary capsule is positioned over the primary capsule and the compressible member. A portion of the secondary capsule is crimped to form a crimp in the secondary capsule that compresses the compressible member against the primary capsule. The crimp secures the secondary capsule to the primary capsule.

Other features and benefits that characterize embodiments of the present disclosure will be apparent upon reading the following detailed description and review of the associated drawings.

BRIEF DESCRIPTION OF THE DRAWINGS

FIGS. 2 and 3 respectively are isometric assembled and exploded views of a probe tip in accordance with embodiments of the invention.

DETAILED DESCRIPTION OF ILLUSTRATIVE EMBODIMENTS

Figure 1:
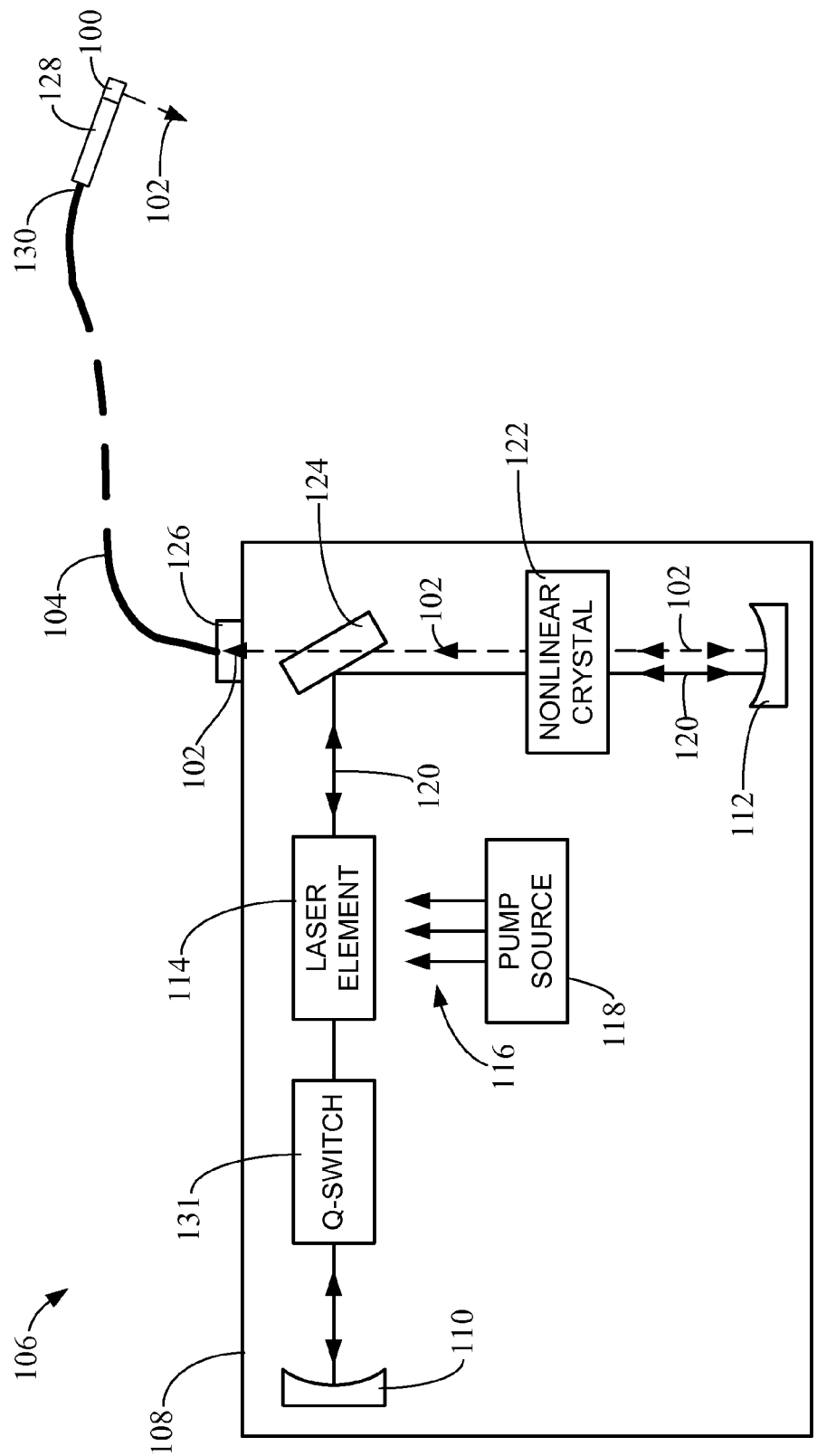
FIG. 1 is a simplified block drawing of an exemplary surgical laser system in accordance with embodiments of the invention.

Embodiments of the invention are directed to an apparatus in the form of a probe tip 100 that is configured to discharge electromagnetic radiation 102 from a waveguide, such as an optical fiber 104, as illustrated in the simplified block diagram of a surgical laser system 106 provided in FIG. 1. The exemplary system 106 comprises a laser resonator 108. The laser resonator 108 may include a first resonator mirror 110, a second resonator mirror 112 and a laser rod or element 114. In one embodiment, the laser element 114 comprises a yttrium-aluminum-garnet crystal rod with neodymium atoms dispersed in the YAG rod to form a Nd:YAG laser element. Other conventional laser elements 114 may also be used.

The laser element 114 is pumped by a light input 116 from an optical pump source 118, such as a Kr arc lamp or other conventional pump source, to produce laser light or beam 120 at a first frequency. The laser resonator 108 also includes a nonlinear crystal 122, such as a lithium borate (LBO) crystal or a potassium titanyl phosphate crystal (KTP), for generating a second harmonic of the laser beam 120 emitted by the laser element 114. The laser beam 120 inside the resonator 108 bounces back and forth between the first and second resonator mirrors 110 and 112, reflects off a folding mirror 124 and propagates through the laser element 114 and nonlinear crystal 122. The laser element 114 has optical gain at a certain wavelength and this determines the wavelength of the laser beam 120 inside the resonator 108. This wavelength is also referred to as the fundamental wavelength. For the Nd:YAG laser element 114, the fundamental wavelength is 1064 nm.

When the laser beam 120 inside the resonator 108 propagates through the nonlinear crystal 122 in a direction away from the folding mirror 124 and toward the second resonator mirror 112, a beam 102 of electromagnetic radiation at the second harmonic wavelength is output from the crystal 122. The second resonator mirror 112 is highly reflective at both the fundamental and second harmonic wavelengths and both beams 120 and 102 propagate back through the nonlinear crystal 122. On this second pass, more beams 102 at the second harmonic wavelength are produced. For example, the nonlinear crystal 122 can produce a laser beam 102 having a wavelength of approximately 532 nm (green) when a Nd:YAG rod is used as the laser element 114. One advantage of the 532 nm wavelength is that it is strongly absorbed by hemoglobin in blood and, therefore, is useful for cutting, vaporizing and coagulating vascular tissue.

The folding mirror 124 is highly reflective at the fundamental wavelength and is highly transmissive at the second harmonic wavelength. Thus, the laser beam 102 at the second harmonic passes through the folding mirror 124 and produces a second harmonic laser beam 102 outside the optical resonator 108. An optical coupler 126 is connected to a waveguide, such as an optical fiber 104, to deliver the laser beam 102 to a laser delivery probe 128 coupled to a distal end 130 of the optical fiber 104. In one embodiment, the probe 128 includes the probe tip 100 formed in accordance with embodiments of the invention that delivers the beam 102 to desired tissue for treating a condition of the patient. In one embodiment, the probe 128 includes an endoscope or cystoscope.

The laser beam 120 inside the resonator 108 at the fundamental wavelength continues through the laser element 114 and reflects off the first resonator mirror 110 which is highly reflective at the fundamental wavelength. A Q-switch 131 may be used in the resonator 108 to change the laser beam 120 to a train of short pulses with high peak power. These short pulses increase the conversion efficiency of the second harmonic laser beam 102 and increase the average power of the laser beam 102 outside the resonator 108.

FIGS. 2 and 3 respectively show isometric assembled and exploded views of a probe tip 100 in accordance with embodiments of the invention. While embodiments of the probe tip 100 are described as being configured to direct the electromagnetic energy 102 laterally relative to a longitudinal axis 132 of the waveguide or optical fiber 104, it should be understood that embodiments of the probe tip 100 include configurations in which the electromagnetic energy is directed in other directions, such as along the longitudinal axis 132 or at alternative angles, for example.

In one embodiment, the probe tip comprises a primary capsule 134 attached to a distal end 130 of the waveguide 104 and a secondary capsule 136 over the primary capsule 134. In one embodiment, the primary capsule in combination with the distal end of the waveguide 104 directs the laser or electromagnetic energy 102 laterally relative to the longitudinal axis 134 of the waveguide 104. The secondary capsule protects the primary capsule during laser treatments.

Figure 4:
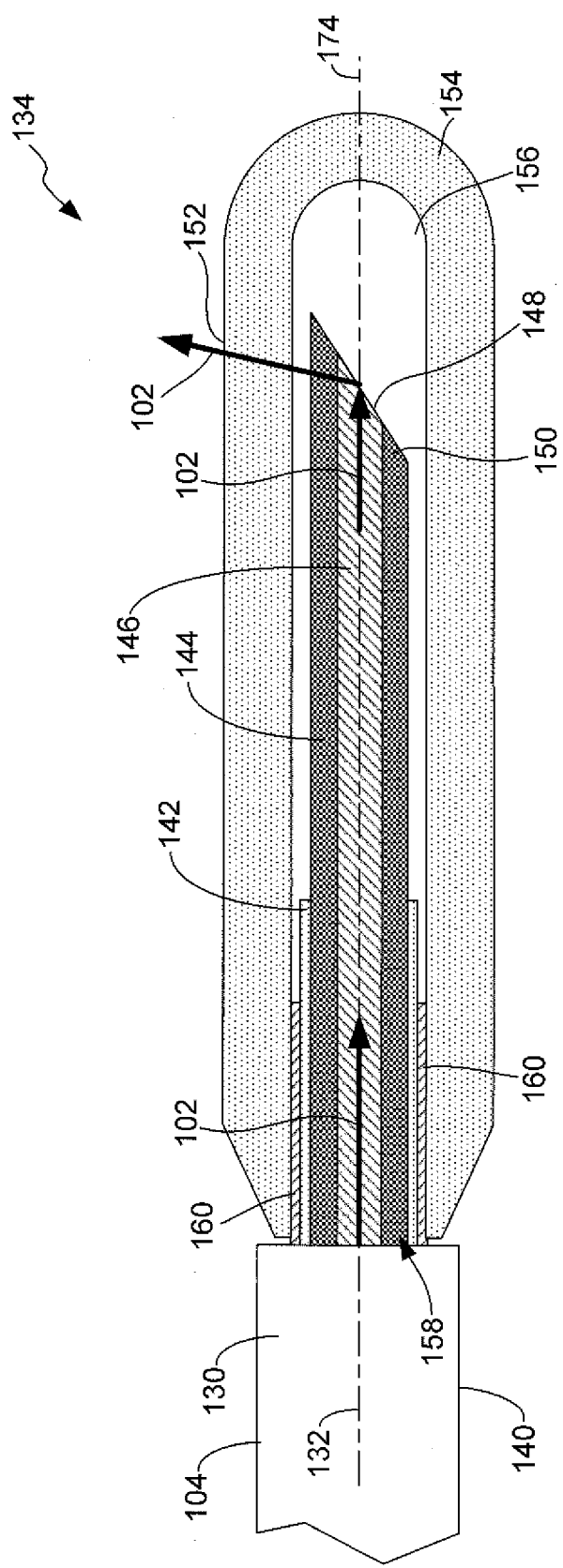
FIG. 4 is a side cross-sectional view of a primary capsule of the probe tip of FIG. 3 taken generally along line 4-4.

FIG. 4 is a side cross-sectional view of the primary capsule 134 and the distal end 130 of the optical fiber 104 shown in FIG. 3 taken generally along line 4-4, in accordance with exemplary embodiments of the invention. Embodiments of the optical fiber 104 generally comprise a nylon jacket 140, a buffer or hard cladding 142, cladding 144 and an optical fiber core 146. It is understood that other forms of optical fibers may also be used. The optical fiber core 146 operates as a waveguide through which electromagnetic energy, such as laser beam 102 (FIG. 1), travels. In one embodiment, the nylon jacket 140 and at least a portion of the hard cladding 142 is removed from the distal end 130 to expose the cladding 144, as illustrated in FIG. 4. In one embodiment, a polished beveled surface 148 is formed at a distal tip 150 of the optical fiber core 146 in accordance with conventional techniques. In one embodiment, the polished beveled surface 148 is non-perpendicular to the longitudinal axis 132 of the optical fiber core 146. Such a beveled surface 148 operates to reflect the laser light 102 laterally through a transmitting surface 152, as shown in FIG. 4. The beveled surface 148 can take on other conventional configurations to direct the output laser beam 102 in a desired direction.

Embodiments of the fiber cap 134 include a cap body 154 having an interior cavity 156 and an opening 158 to the interior cavity 156. The distal tip 150 of the optical fiber core 146 is received within the interior cavity 156 through the opening 158. In one embodiment, the cap body 154 seals the interior cavity 156 except at the opening 158. The gas (or vacuum) interface formed at the beveled surface 148 promotes total internal reflection of the beam 102 to direct the beam 102 through the transmitting surface 152.

In one embodiment, the cap body 154 is bonded to the optical fiber 104 by fusing the silica glass cap 134 to the glass cladding 144. Alternatively, the cap body 154 is adhered to the optical fiber 104 using a suitable adhesive 160, such as a silicone or fluorocarbon polymer adhesive, as shown in FIG. 4.

Figure 5:
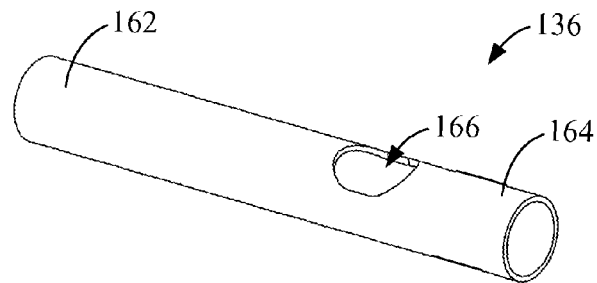
FIGS. 5 and 6 are isometric views of the secondary capsule formed in accordance with embodiments of the invention.
Figure 6:
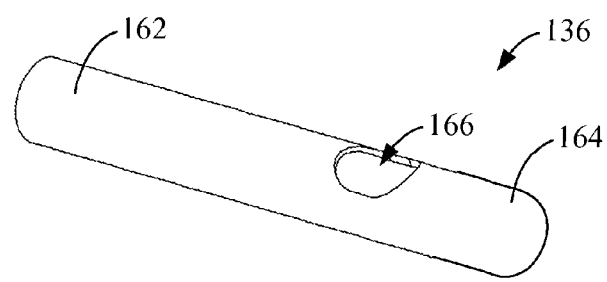

FIGS. 5 and 6 are isometric views of the secondary capsule 136 formed in accordance with embodiments of the invention. In one embodiment, the secondary capsule 136 is formed of a malleable material. In one embodiment, the secondary capsule 136 is formed of metal, such as stainless steel, aluminum, or other suitable metal. In one embodiment, the secondary capsule 136 is a tubular sleeve having an open proximal end 162 and an open distal end 164, as shown in FIG. 5. In one embodiment, the distal end 164 of the capsule is closed, as illustrated in FIG. 6.

Figure 7:
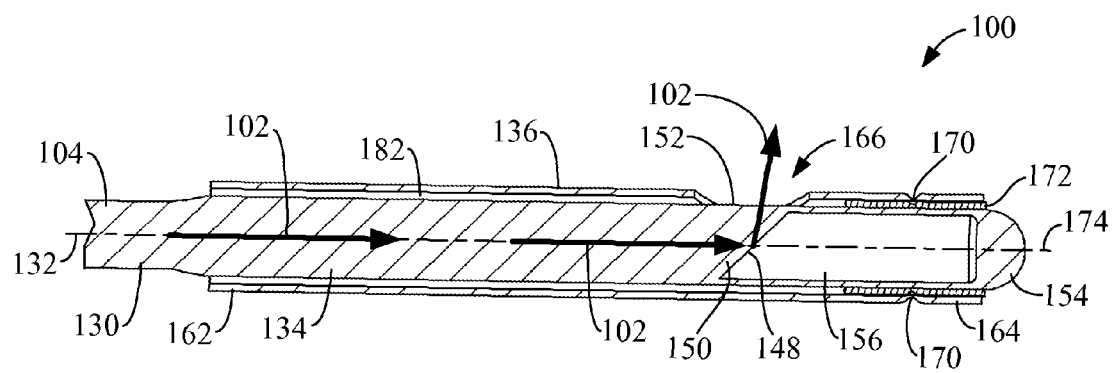
FIG. 7 is a cross-sectional view of the probe tip of FIG. 2 taken generally along line 7-7.

FIG. 7 is a cross-sectional view of the probe tip 100 taken generally along lines 7-7 of FIG. 2. Details of the primary capsule 134 and the optical fiber 104 are not shown in FIG. 7 and other cross-sectional views in order to simplify the illustrations. In one embodiment, the secondary capsule 136 is placed over the primary capsule 134 such that the proximal end 162 of the capsule 136 is located on a proximal side of the distal tip 150 of the waveguide 104, and the distal end 164 of the capsule 136 is on a distal side of the distal tip 150. In one embodiment, an output port 166 in the secondary capsule 136 is aligned with the transmissive surface 152. In operation, electromagnetic energy 102 that is reflected off the beveled surface 148 travels through both the transmissive surface 152 and the opening 158.

Figure 8:
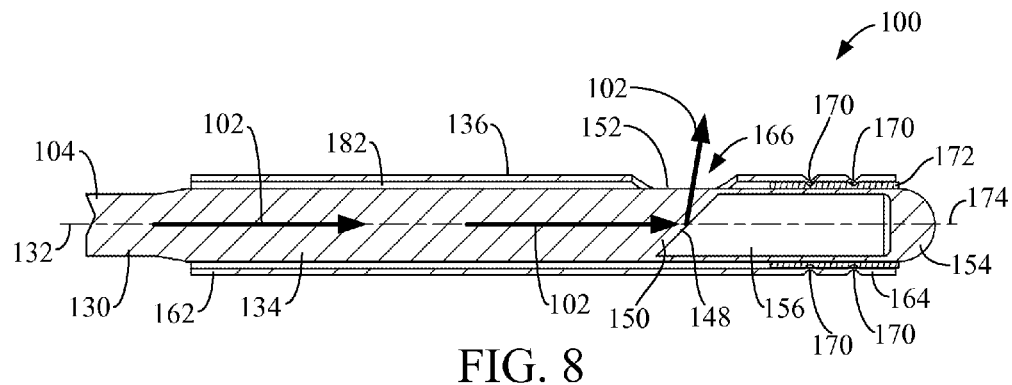
FIG. 8 is a side cross-sectional view of a probe tip in accordance with embodiments of the invention.

In one embodiment, the secondary capsule 136 is secured to either the primary capsule 134 and/or the optical fiber 104 by way of one or more crimps 170 in the secondary capsule 136, as shown in the cross-sectional views of the probe tip 100 provided in FIGS. 7 and 8. As used herein, the crimps 170 are formed by creating a deformation, such as a dent, in the secondary capsule 136 that extends toward the primary capsule 134. In one embodiment, the crimp is formed by squeezing the secondary capsule.

In one embodiment, the probe tip 100 includes a compressible member 172 (FIGS. 3 and 7) that is positioned between the primary capsule 134 and the secondary capsule 136 such that the compressible member 172 covers a portion of the primary capsule 134. In one embodiment, the compressible member 172 generally fills a gap between the inner diameter of the secondary capsule 136 and the outer diameter of the primary capsule 134. The one or more crimps 170 operate to compress the compressible member 172 against the primary capsule 134 to secure the secondary capsule 136 to the primary capsule 134.

The compressible member 172 may be formed of any suitable material, such as silicone. In one embodiment, the compressible member 172 comprises a compressible sleeve (FIG. 3) that is placed over the primary capsule 134. Alternatively, the distal end of the primary capsule 134 may be dip coated in silicone or other compressible material to form the compressible member 172 thereon.

In one embodiment, the one or more crimps 170 comprise annular crimps that are generally coaxial to the longitudinal axis 174 of the primary capsule 134, as shown in FIGS. 2, 7 and 8. That is, one embodiment of the crimps 170 comprises an annular dent in the secondary capsule 136 that extends toward the primary capsule 134. In one embodiment, the one or more crimps 170 may comprise one or more segmented deformations of the secondary capsule 136 that extend toward the primary capsule 134. In one embodiment, the one or more crimps 170 are formed on the distal end 164 of the secondary capsule 136, as shown in FIGS. 2, 7 and 8. That is, the crimps 170 are formed on a distal side of the beveled surface 148 and the output port 166. In one embodiment, the capsule 136 does not include crimps 170 on the proximal end 162.

Figure 9:
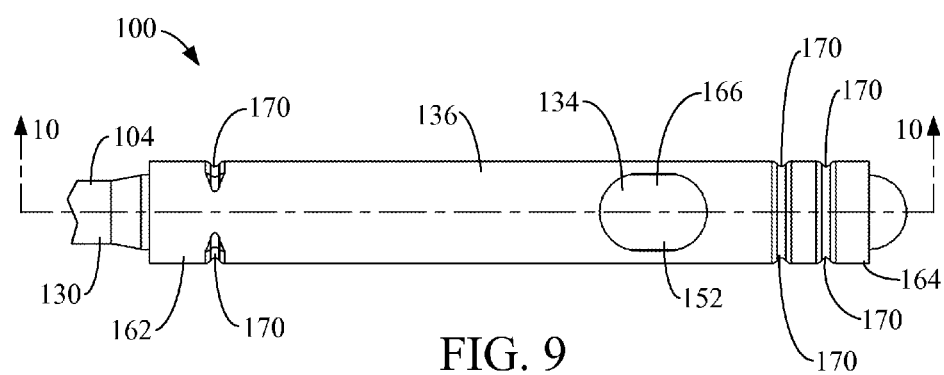
FIG. 9 is a top view of a probe tip formed in accordance with embodiments of the invention.

FIG. 9 is a top view of a probe tip 100 formed in accordance with embodiments of the invention. In one embodiment, the one or more crimps 170 are formed only on the proximal end 162 of the capsule 136. That is, the crimps 170 are formed on the proximal side of the beveled surface 148 and the output port 166, and the distal end 164 does not include any crimps 170. In one embodiment, the one or more crimps 170 are formed on both the proximal end 162 and the distal end 164 of the capsule 136, as shown in FIG. 9. Thus, the crimps 170 may be formed both on the proximal and distal sides of the beveled surface 148 and the output port 166.

Figure 10:
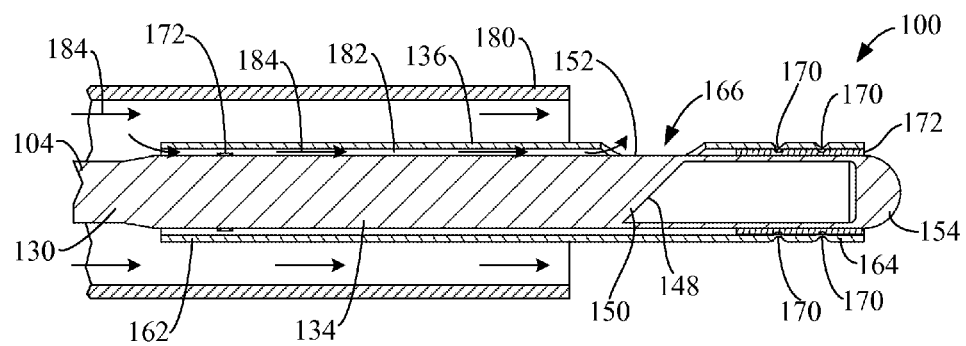
FIG. 10 is a cross-sectional view of the probe tip of FIG. 9 taken generally along line 10-10 and located within a fluid flow channel.

In one embodiment, the probe tip 100 is configured to be placed within a fluid flow channel during laser treatment operations to assist in preventing the primary capsule 134 from overheating, which could lead to a failure. FIG. 10 is a cross-sectional view of the probe tip of FIG. 9 taken generally along line 10-10 and located within a fluid flow channel 180. Embodiments of the fluid flow channel 180 include fluid channels formed in endoscopes, cystoscopes or other devices.

In one embodiment, the probe tip 100 includes a fluid flow channel 182 between the primary capsule 134 and the secondary capsule 136 that extends from the proximal end 162 to the output port 166, as shown in FIGS. 7, 8 and 10. The fluid flow channel 182 allows fluid (represented by arrows 184) in the channel 180 to travel between the primary capsule 134 and the secondary capsule 136. For instance, fluid may enter the channel 182 at the proximal end 162 and exit at the output port 166, as illustrated in FIG. 10. The flow of the fluid through the channel 182 acts to cool the primary capsule 134 and to irrigate the area around the transmissive surface 152. In one embodiment, the fluid flow channel 182 extends between adjacent deformations of the one or more crimps 170 formed at the proximal end 162, as shown in FIG. 10.

Figure 11:
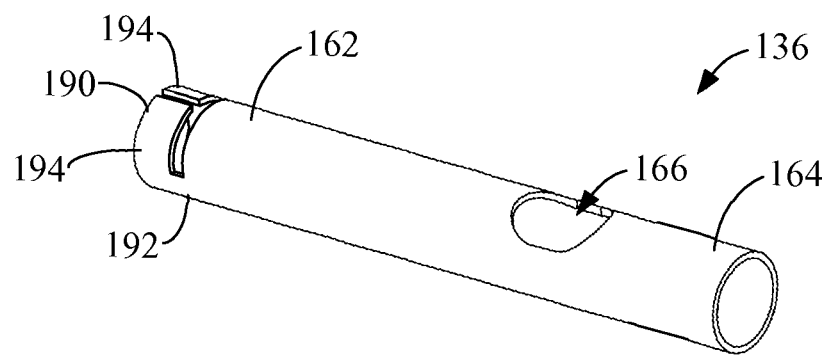
FIGS. 11 and 12 are isometric views of a secondary capsule formed in accordance with embodiments of the invention.
Figure 12:
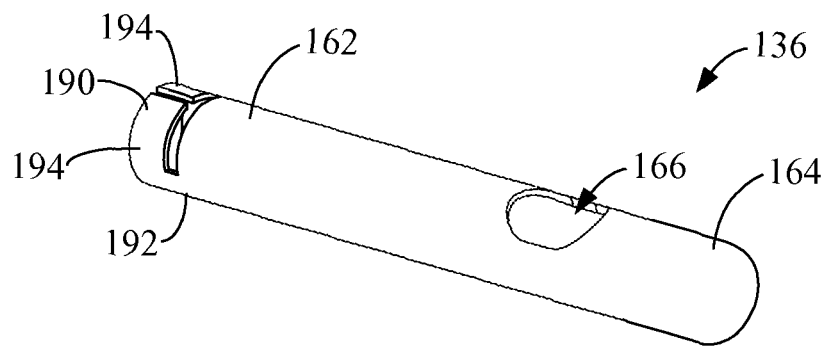

FIGS. 11 and 12 are isometric views of the secondary capsule 136 formed in accordance with embodiments of the invention. As previously discussed, embodiments of the capsule 136 comprise a tubular sleeve of malleable material, such as metal, having an open proximal end 162 and either an open distal end 164 (FIG. 11) or a closed distal end 164 (FIG. 12). Elements having the same or similar labels correspond to the same or similar elements as those discussed above.

Figure 13:
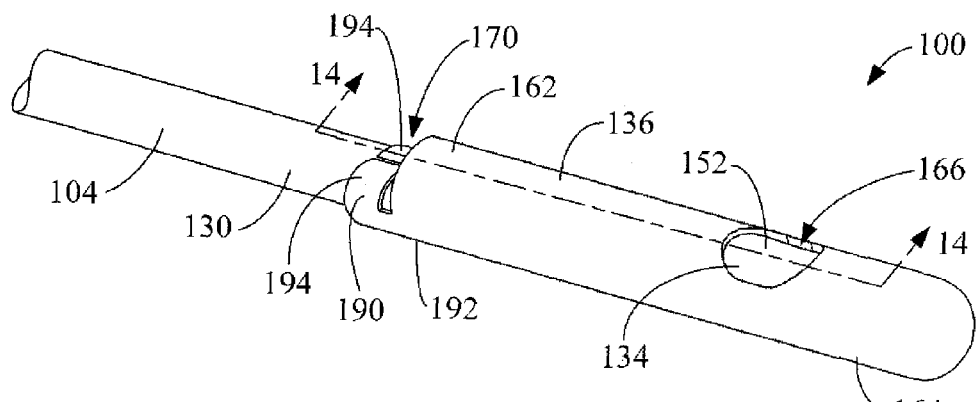
FIG. 13 is an isometric view of a probe tip formed in accordance with embodiments of the invention.
Figure 14:
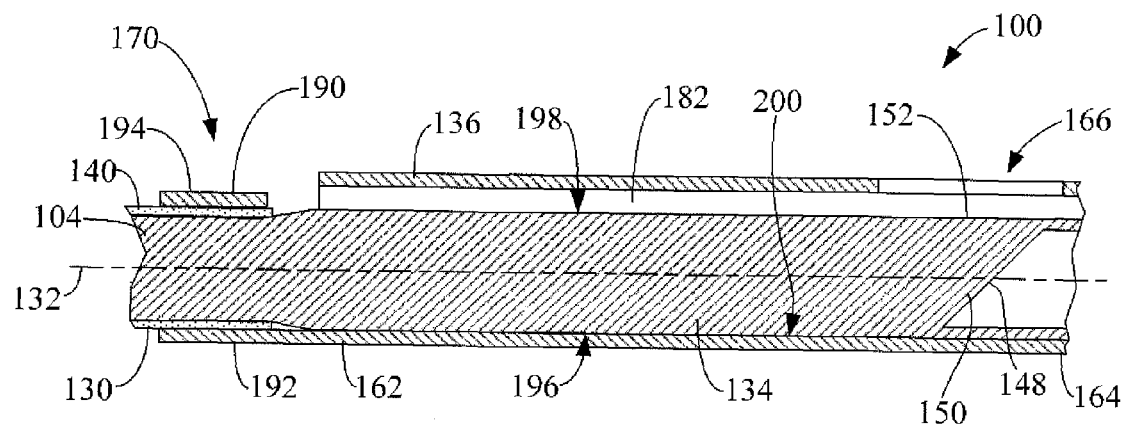
FIG. 14 is a cross-sectional view of the probe tip illustrated in FIG. 13 taken generally along line 14-14.

In one embodiment, the secondary capsule includes a crimp 170 at the proximal end 162 that compresses a protective layer of the waveguide or optical fiber 104, as shown in FIGS. 13 and 14, which respectively are an isometric view of the probe tip 100 and a cross-sectional view of the probe tip 100 illustrated in FIG. 13 taken generally along line 14-14. The crimp 170 operates to secure the position of the secondary capsule 136 relative to the primary capsule 134. In one embodiment, the protective layer of the optical fiber 104 that is compressed by the crimp 170 may be the nylon jacket 140, the buffer or hard cladding 142, or other component of the optical fiber 104. In one embodiment, the protective layer compressed by the crimp 170 is the outer layer of the waveguide or optical fiber 104, such as the nylon jacket 140, as shown in FIG. 14.

In one embodiment, the secondary capsule 136 includes one or more deformable members 190 at the proximal end 162 that are used to form the crimp 170. In one embodiment, the one or more deformable members 190 extend from a backside 192 of the proximal end 162 of the capsule 136, as best shown in FIG. 14. In one embodiment, the one or more deformable members 190 each comprise a tab 194 extending from the backside 192 of the capsule 136. Each tab 194 may be bent toward the backside 192 to compress the optical fiber 104 against the backside 192, as shown in FIGS. 13 and 14.

In one embodiment, the probe tip 100 includes a fluid flow channel 182 extending from the proximal end 162 to the output port 166, as shown in FIG. 14. In one embodiment, a backside 196 of the primary capsule 134, which is opposite a front side 198 that comprises the transmissive surface 152, is pressed against an interior surface 200 of the backside 192 of the secondary capsule 136, as shown in FIG. 14. By positioning the primary capsule 134 against the backside 192 of the secondary capsule 136, a gap is formed between the front side 198 of the primary capsule 134 and the secondary capsule 136 that forms the fluid flow channel 182. As a result, fluid is allowed to flow into the channel 182 from the proximal end 162 and exit through the output port 166 when placed in a fluid flow channel, such as channel 180 shown in FIG. 10.

Figure 15:
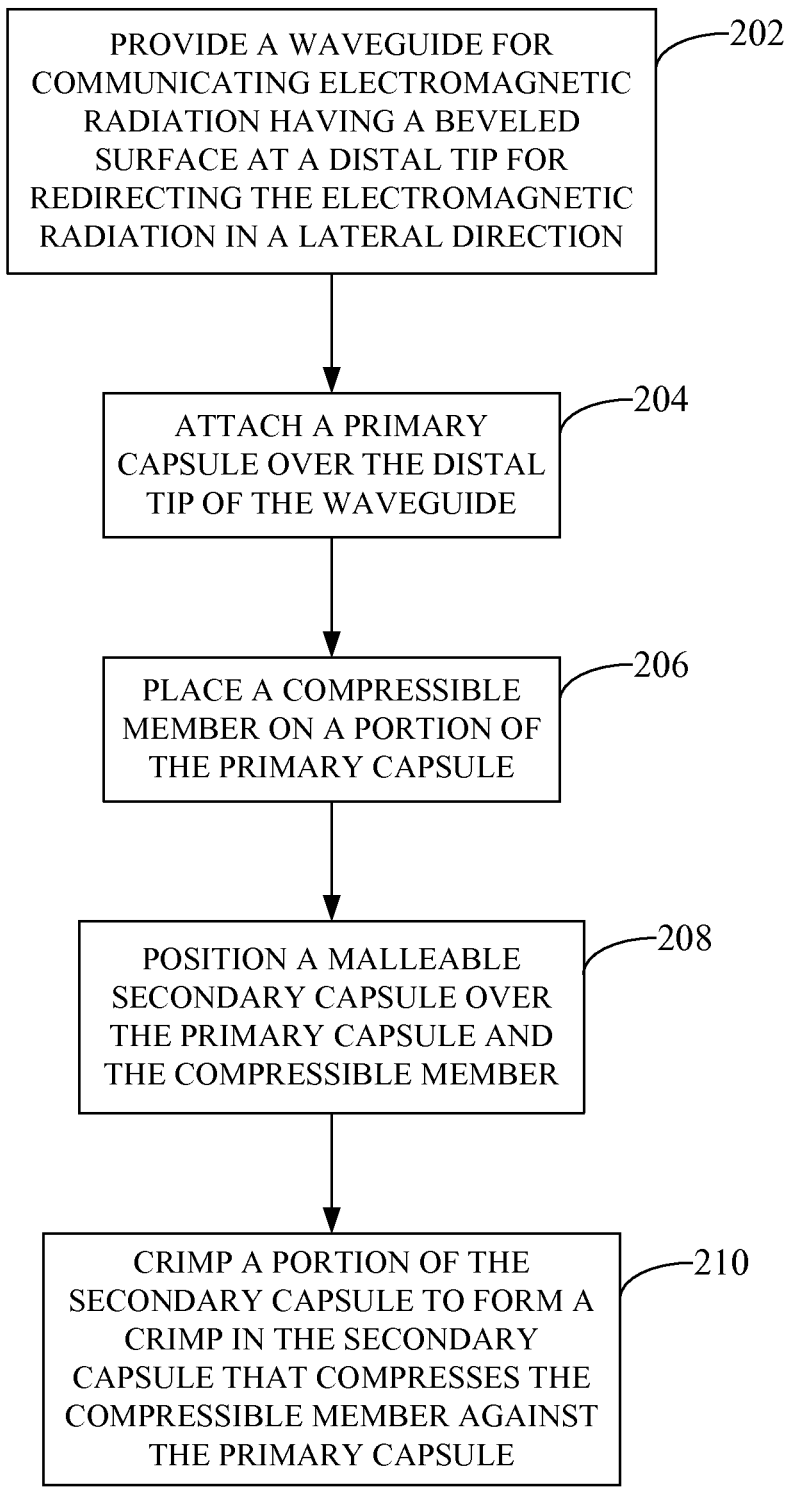
FIG. 15 is a flowchart illustrating a method in accordance with embodiments of the invention.

FIG. 15 is a flowchart illustrating a method in accordance with embodiments of the invention. Another embodiment of the invention is directed to a method. At 202, a waveguide 104, such as an optical fiber, is provided for communicating electromagnetic radiation. The waveguide 104 includes a beveled surface 148 at a distal tip 150 for redirecting the electromagnetic radiation in a lateral direction relative to a longitudinal axis 132 of the waveguide 104. At 204, a primary capsule 134 is attached over the distal tip 150 of the waveguide 104, as shown in FIG. 4. At 206, a compressible member 172 (FIGS. 3 and 7) is then placed on a portion of the primary capsule 134. A malleable secondary capsule 136 is then positioned over the primary capsule 134 and the compressible member 172, at 208. At 210, a portion of the secondary capsule is crimped to form a crimp 170 that compresses the compressible member 172 against the primary capsule 134. The crimp 170 secures the secondary capsule 136 to the primary capsule 134.

In one embodiment of the method, the secondary capsule 136 has a proximal end 162 on a proximal side of the distal tip 150 and a distal end 164 on a distal side of the distal tip 150. One embodiment of the crimping step 210 comprises crimping a portion of the distal end 164 of the secondary capsule.

In one embodiment, the primary capsule 134 includes a transmissive surface 152 through which the laterally directed electromagnetic radiation is discharged. The secondary capsule includes an output port 166 that is aligned with the transmissive surface 152. In the method, a fluid flow channel 182 is formed between the primary capsule 134 and the secondary capsule 136 that extends from a proximal end 162 of the secondary capsule 136 to the output port 166.

In one embodiment of the method, step 206 is not performed and the crimping step 210 involves crimping a deformable member 190 at the proximal end 162 to form a crimp 170 that compresses a protective layer of the waveguide or optical fiber 104, as discussed above with regard to FIGS. 11-14. The crimp 170 secures the position of the secondary capsule 136 over the primary capsule 134.

Although the present invention has been described with reference to preferred embodiments, workers skilled in the art will recognize that changes may be made in form and detail without departing from the spirit and scope of the invention.

What is claimed is:

1. An apparatus comprising:
    a waveguide for communicating electromagnetic radiation, the waveguide comprising a core having a distal tip;
    a primary capsule included over the distal tip of the waveguide, the primary capsule having a proximal end and a distal end;
    a secondary capsule over the primary capsule, the secondary capsule comprising an outlet port, a proximal end on a proximal side of the distal tip of the waveguide, a distal end on a distal side of the distal tip of the waveguide, and a crimp on the proximal end of the secondary capsule to secure the secondary capsule to the waveguide; and
    a fluid flow channel between the primary capsule and the secondary capsule extending from the proximal end of the secondary capsule to the output port.

2. The apparatus of claim 1, wherein the waveguide comprises a protective layer and the crimp compresses the protective layer.

3. The apparatus of claim 2, wherein the crimp comprises at least one tab for compressing the protective layer.

4. The apparatus of claim 2, wherein the protective layer comprises a nylon jacket, and the crimp compresses the nylon jacket.

5. The apparatus of claim 1, wherein:
    the primary capsule includes a transmissive surface through which the electromagnetic radiation is discharged; and
    the output port is aligned with the transmissive surface.

6. The apparatus of claim 1, wherein:
    a back side of the primary capsule, which is opposite a front side of the primary capsule, is pressed against a back side of the secondary capsule; and
    the fluid flow channel is formed between the front side of the primary capsule and a front side of the secondary capsule.

7. The apparatus of claim 1, wherein the secondary capsule is formed of a malleable metal.

8. The apparatus of claim 1, wherein the distal tip of the core includes a polished surface that is beveled for redirecting the electromagnetic radiation laterally.

9. An apparatus comprising:
    an optical fiber comprising a core for communicating the electromagnetic radiation, the core comprising a distal portion configured to direct electromagnetic radiation out of the optical fiber;
    a primary capsule included over the distal portion of the core;
    a secondary capsule over the primary capsule, the secondary capsule comprising an outlet port adjacent the distal portion of the core and a proximal end including a crimp that secures the position of the secondary capsule relative to the primary capsule; and
    a fluid flow channel between the primary capsule and the secondary capsule extending from the proximal end of the secondary capsule to the output port.

10. The apparatus of claim 9, wherein:
    the secondary capsule includes a deformable member extending from the back side of the proximal end; and
    the crimp is formed by the deformable member.

11. The apparatus of claim 10, wherein the deformable member comprises at least one tab for compressing a protective layer included on at least a portion of the waveguide.

12. The apparatus of claim 9, wherein:
the waveguide includes a protective layer surrounding the core; and
the crimp compresses the protective layer.

13. The apparatus of claim 9, wherein:
a back side of the primary capsule, which is opposite a front side of the primary capsule, is pressed against a back side of the secondary capsule; and
the fluid flow channel is formed between the front side of the primary capsule and a front side of the secondary capsule.

14. The apparatus of claim 9, wherein the distal portion of the core includes a polished distal surface that is beveled for redirecting the electromagnetic radiation laterally through the outlet port.

15. An apparatus comprising:
an optical fiber comprising a core and a protective layer surrounding the core, the core comprising a distal tip that extends beyond the protective layer;
a primary capsule included over the distal tip of the core, the primary capsule having a front side and a back side opposite the front side;
a secondary capsule over the primary capsule and comprising:
a proximal end including a crimp that compresses the protective layer of the optical fiber and secures the position of the secondary capsule relative to the primary capsule; and
an outlet port,
wherein the back side of the primary capsule is pressed against a back side of the secondary capsule; and
a fluid flow channel extending from the proximal end of the secondary capsule to the output port between the front side of the primary capsule and the front side of the secondary capsule.

16. The apparatus of claim 15, wherein the protective layer comprises a nylon jacket.

17. The apparatus of claim 16, wherein the crimp compresses the nylon jacket.

18. The apparatus of claim 15, wherein:
the primary capsule includes a transmissive surface through which the electromagnetic radiation is discharged; and
the core comprises a polished beveled surface for redirecting the electromagnetic radiation laterally through the transmissive surface and the outlet port.

19. The apparatus of claim 15, wherein:
the secondary capsule includes a deformable member extending from the back side of the proximal end; and
the crimp is formed by the deformable member.

20. The apparatus of claim 19, wherein the deformable member comprises at least one tab for compressing the protective layer.

21. A method of performing a laser treatment using the apparatus of claim 9 comprising the steps of:
transmitting the electromagnetic radiation through the core;
discharging the electromagnetic radiation through the primary capsule and the outlet port; and
driving fluid through the fluid flow channel.

22. The method of claim 21, wherein driving fluid through the fluid flow channel includes driving fluid into the fluid flow channel at the proximal end of the secondary capsule and out the outlet port.

23. The method of claim 22, wherein driving fluid through the outlet port and discharging the electromagnetic radiation occurs simultaneously.

24. A method comprising the steps of:
providing a waveguide for communicating the electromagnetic radiation, the waveguide comprising a core having a distal tip and a protective layer;
removing a portion of the protective layer from a distal portion of the waveguide;
attaching a primary capsule over the distal tip of the waveguide;
positioning a secondary capsule over the primary capsule and a portion of the protective layer not removed from the waveguide, the secondary capsule comprising a proximal end on a proximal side of the distal tip of the waveguide and a distal end on a distal side of the distal tip of the waveguide; and
crimping the proximal end of the secondary capsule onto at least a portion of the protective layer not removed from the waveguide to secure the position of the secondary capsule relative to the primary capsule.

25. The method of claim 24, wherein the proximal end of the secondary capsule comprises at least one tab for compressing the protective layer.

26. The method of claim 24, wherein the protective layer comprises a nylon jacket and crimping the proximal end of the secondary capsule compresses the nylon jacket.

* * * * *